United States Patent [19]
Brazdil, Jr. et al.

[11] Patent Number: 6,156,920
[45] Date of Patent: Dec. 5, 2000

[54] MOLYBDENUM PROMOTED VANADIUM-ANTIMONY-OXIDE BASED CATALYST FOR SELECTIVE PARAFFIN AMMOXIDATION

[75] Inventors: James Frank Brazdil, Jr., Highland Heights; Mark Anthony Toft, Lakewood, both of Ohio

[73] Assignee: The Standard Oil Company, Chicago, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 09/048,648

[22] Filed: Mar. 26, 1998

[51] Int. Cl.$^7$ .................................................. C07C 253/00
[52] U.S. Cl. ......................... 558/319; 502/338; 502/350; 502/352; 502/353
[58] Field of Search .................... 502/338, 350, 502/352, 353; 558/319

[56] References Cited

U.S. PATENT DOCUMENTS 5,008,427  4/1991  Brazdil et al. ........................ 558/319

*Primary Examiner*—Johann Richter
*Assistant Examiner*—Joseph Murray
*Attorney, Agent, or Firm*—David P. Yusko

[57] ABSTRACT

A process of manufacturing acrylonitrile or methacrylonitrile by the catalytic reaction in the vapor phase of a paraffin selected from propane and isobutane with molecular oxygen and ammonia by catalytic contact of the reactants in a reaction zone with a catalyst, the feed composition having a mole ratio of the paraffin to ammonia in the range of from about 2.5 to 16 and a mole ratio of paraffin to oxygen in the range of from about 1.0 to 10, wherein said catalyst has the elements in the proportions indicated by the empirical formula:

$$VSb_mA_aMo_bD_dO_x$$

where
A is one or more of Ti, Sn, Fe, Cr and Ga;
D is one or more of Li, Mg, Ca, Sr, Ba, Co, Ni, Zn, Ge, Nb, Zr, W, Cu, Te, Ta, Se, Bi, Ce, In, As, B and Mn;
m equals 0.8 to 4;
a equals 0.01 to 2;
0<b<0.005;
d is 0 to 2;
x is determined by the oxidation state of the cations present, and the catalyst has been heat treated at a temperature of at least 780° C.

12 Claims, No Drawings

MOLYBDENUM PROMOTED VANADIUM-ANTIMONY-OXIDE BASED CATALYST FOR SELECTIVE PARAFFIN AMMOXIDATION

BACKGROUND OF THE INVENTION

Field of the Invention

This invention relates to an improved catalyst for the ammoxidation of propane and isobutane to $\alpha,\beta$-unsaturated mononitriles (acrylonitrile and methacrylonitrile). The preferred application of the invention is in the recycle process in which unreacted propane and isobutane, along with propylene and isobutene produced by the reaction, are recycled back to the reactor for the conversion to acrylonitrile and methacrylonitrile.

Nitriles, such as acrylonitrile and methacrylonitrile, have been synthetic resins, synthetic rubbers and the like. The commercially dominant method for their production requires the ammoxidation of propylene or isobutylene in the presence of ammonia and oxygen at a high temperature in a gas phase in the presence of an ammoxidation catalyst.

However, in view of the price differential between propane and propylene, or the price difference between isobutane and isobutene, recent attention has been drawn to the development of a method and catalyst for the production of acrylonitrile or methacrylonitrile by an ammoxidation reaction wherein the lower alkane such as propane or isobutane is used as a starting material and such lower alkane is catalytically reacted with ammonia and an oxygen-containing gas in the presence of a catalyst.

Earlier attempts to develop an efficient process for the ammoxidation of propane to acrylonitrile produce either insufficient yields or processes that necessitated adding halogen promoters to the feed. The latter procedure would require not only reactors made of special corrosion resistant materials, but also a quantitative recovery of the promoter. This added cost eliminated the advantages of the propane/propylene price differential.

Recent patent publications such as EPO O 767164-A1 and patents such as U.S. Pat. No. 5,008,427 have been directed to ammoxidation catalyst systems which are directed to solving the problems of previous attempts at propane ammoxidation using specific catalyst. In particular, U.S. Pat. No 5,008,427 assigned to the assignees of the present invention is specifically directed to a vanadium-antimony promoted catalyst for propane ammoxidation wherein the catalyst is calcined at temperatures of 780° C. or higher. The catalyst in the present invention and the ammoxidation procedure disclosed herein is directed to an improvement in the '427 patent.

SUMMARY OF THE INVENTION

It is an object of the present invention to provide an improved process for the ammoxidation of paraffins to unsaturated mononitriles and the corresponding monoolefins.

It is a further object of the present invention to provide an improved catalytic ammoxidation process for making unsaturated mononitriles from lower paraffins without the necessity of using halogen promoters.

It is a still further object in the present invention to provide a process for making a vanadium-antimony promoted oxide catalyst which during calcination, at temperatures of 780° C. or higher, activates the catalyst and minimizes or eliminates clumping together of the catalyst to make larger catalyst particles.

It is another object of the present invention to provide an improved catalyst for use in the ammoxidation of lower paraffins to the corresponding mononitriles and the corresponding monoolefins.

Other objects as well as aspects, features and advantages of the present invention will become apparent from the study of the accompanying disclosure and the claims.

To achieve the foregoing objects and advantages the process of the present invention comprises an $\alpha,\beta$-unsaturated mononitrile, acrylonitrile or methacrylonitrile by the catalytic reaction in the vapor phase of a paraffin selected from propane and isobutane with molecular oxygen and ammonia by catalytic contact of the reactants in a reaction zone with a catalyst, the feed composition having a mole ratio of the paraffin to ammonia in the range of from about 2.5 to 16 and a mole ratio of paraffin to oxygen in the range of from about 1.0 to 10, wherein said catalyst has the elements in the proportions indicated by the empirical formula:

$$VSb_mA_aMo_bD_dO_x$$

where

A is one or more of Ti, Sn, Fe, Cr and Ga;

D is one or more of Li, Mg, Ca, Sr, Ba, Co, Ni, Zn, Ge, Nb, Zr, W, Cu, Te, Ta, Se, Bi, Ce, In, As, B and Mn;

m equals 0.8 to 4;

a equals 0.01 to 2;

0<b<0.005;

d is 0 to 2;

x is determined by the oxidation state of the cations present, and the catalyst has been heat treated at a temperature of at least 780° C.

It is another aspect of the present invention to manufacture a promoted vanadium-antimony oxide catalyst which is characterized by being substantially free of clumping by a process comprising heat treating a vanadium-antimony oxide catalyst including at least one or more of the A element and molybdenum at a calcination temperature of at least 780° C. and higher is used.

DETAILED DESCRIPTION OF THE INVENTION

According to one aspect of the invention there is provided a process for making an $\alpha,\beta$-unsaturated mononitrile, acrylonitrile or methacrylonitrile by the catalytic reaction in the vapor phase of a paraffin selected from propane and isobutane with molecular oxygen and ammonia by catalytic contact of the reactants in a reaction zone with a catalyst, the feed composition having a mole ratio of the paraffin to ammonia in the range of from about 2.5 to 16 and a mole ratio of paraffin to oxygen in the range of from about 1.0 to 10, wherein said catalyst has the elements in the proportions indicated by the empirical formula:

$$VSb_mA_aMo_bD_dO_x$$

where

A is one or more of Ti, Sn, Fe, Cr and Ga;

D is one or more of Li, Mg, Ca, Sr, Ba, Co, Ni, Zn, Ge, Nb, Zr, W, Cu, Te, Ta, Se, Bi, Ce, In, As, B and Mn;

m equals 0.8 to 4;

a equals 0.01 to 2;

b is greater than zero up to 0.05;

d is 0 to 2;

x is determined by the oxidation state of the cations present, and the catalyst has been heat treated at a temperature of at least 780° C.

Calcination temperatures can be as high as 1200° C. However, calcination temperatures are usually in the range of from about 790° to 1050° C. The calcination temperature can vary from composition to composition but the particular calcination temperature utilized for a given composition can be determined easily by routine experimentation.

Similar to the disclosure in U.S. Pat. No. 5,008,427, herein incorporated by reference, it has been found that it is preferable that subscript m in the empirical formula set forth above usually provides the best results when it is at least 1.2 and when it is at most 2.0.

It is also preferred that subscript a as defined above is at least 0.05 and that it preferably does not exceed 0.5 or even 0.4. In a further preferred embodiment element A includes one or more of tin, titanium and iron.

It is particularly important to note that applicants have discovered that molybdenum must be present in the catalyst and within the specific range disclosed in the empirical formula to obtain the improved results disclosed in the examples set forth below in Table I. Preferably, the molybdenum ranges from greater than zero to 0.0045, more preferably greater than zero to 0.0035, especially preferred being greater than zero to 0.0030.

Typical reaction conditions for the ammoxidation of the propane or isobutane to acrylonitrile and methacrylonitrile are set forth in U.S. Pat. No. 5,008,427 described above and herein incorporated by reference. The reaction temperature range can vary from 350° to 700° C., but is usually between 430° to 520° C. The average contact time can often be from 0.01 to 10 seconds but is usually between 0.02 to 10 seconds and more, preferably between 0.1 to 5 seconds. The pressure in the reaction zone usually ranges from 2 to 75, but is preferably no more than 50 psia.

In a further preferred embodiment of the present invention, reaction takes place in a fluid bed reactor which is equipped for recycle of the unreacted propane and generated propylene back into the fluid bed reactor.

In order to make the vanadium-antimony oxide catalyst described in the present invention so that clumping of the catalyst composition particles is eliminated or substantially reduced during heat treatment a calcination temperature of 780° C. and higher is used, and include one or more of the required A elements in the vanadium-antimony oxide catalyst composition along with the required molybdenum element. Optionally, one may include one or more of the D elements in amounts such that the composition contains the elements and the proportions indicated by the empirical formula set forth below:

where

A is one or more of Ti, Sn, Fe, Cr and Ga;

D is one or more of Li, Mg, Ca, Sr, Ba, Co, Ni, Zn, Ge, Nb, Zr, W, Cu, Te, Ta, Se, Bi, Ce, In, As, B and Mn;

m equals 0.8 to 4;

a equals 0.01 to 2;

0<b<0.005;

d is 0 to 2;

x is determined by the oxidation state of the cations present, and the catalyst has been heat treated at a temperature of at least 780° C.

In a preferred embodiment of the present invention m equals 1.1 to 1.8; a equals 0.05 to 0.3 and d equals 0 to 0.1.

The examples set forth below are for illustration purposes only and should not be considered as limiting the scope of the invention.

The run conditions in all the examples were at 15 psig, and at a temperature of 480° C., except in Example 15, where the temperature was 475° C. The catalysts were tested for propane ammoxidation using a titanium U-tube microreacter.

EXAMPLES

Catalyst A (Comparative)

27.286 g of $V_2O_5$ powder were added to a solution consisting of 100 ml of 30 wt. % $H_2O_2$ in 900 ml of water in a two liter beaker. After reaction of the $V_2O_5$ powder with $H_2O_2$ was complete, 69.965 g of $Sb_2O_3$ were added followed by 0.959 g of $TiO_2$. The beaker was covered with a watch glass and the mixture was stirred and heated for about 3 hours. Then 4.336 g of 20.9 wt % $SnO_2$ sol prepared by dispersing $SnO_2 \cdot xH_2O$ (metastannic acid) in an aqueous solution of tetramethyl ammonium hydroxide were added. Then 14.372 g of $Fe_2O_3$ powder were added followed by 88.10 g of 32.2 wt % $SiO_2$ sol. The mixture was stirred in an uncovered beaker with heating in order to reduce the volume by evaporation of water. When the mixture could no longer be stirred, it was dried in an oven at 120° C. Thereafter it was calcined for 3 hours at 325° C., 3 hours at 820° C. then at 650° C. for an additional 3 hours. The calcined catalyst, having particle sizes between 20 and 35 mesh, was then contacted with isobutanol in a coarse glass frit funnel by allowing the isobutanol to pass through the funnel without suction. After washing with isobutanol, the catalyst was heated in an oven at 120° C. to remove the residual isobutanol.

Catalyst B (Invention)

Molybdenum was added to Catalyst A using the incipient wetness method by taking 3 g of Catalyst A and uniformly wetting it with 1.1 ml of a 10 ml solution containing 0.0162 g of $(NH_4)_6Mo_7O_{24} \cdot 4H_2O$. The treated catalyst was dried at 120° C. then heat treated at 325° C. for 3 hours.

Catalyst C (Invention)

Molybdenum was added to Catalyst A using the incipient wetness method by taking 2.8 g of Catalyst A and uniformly wetting it with 1.0 ml of a 10 ml solution containing 0.0273 g of $(NH_4)_6Mo_7O_{24} \cdot 4H_2O$. The treated catalyst was dried at 120° C. then heat treated at 325° C. for 3 hours.

Catalyst D (Invention)

27.286 g of $V_2O_5$ powder were added to a solution consisting of 100 ml of 30 wt % $H_2O_2$ in 900 ml of water in a two liter beaker. After reaction of the $V_2O_5$ powder with $H_2O_2$ was complete, 69.965 g of $Sb_2O_3$ were added followed by 0.959 g of $TiO_2$. The beaker was covered with a watch glass and the mixture was stirred and heated for about 3 hours. Then 4.336 g of 20.9 wt % $SnO_2$ sol prepared by dispersing $SnO_2 \cdot xH_2O$ (metastannic acid) in an aqueous solution of tetramethyl ammonium hydroxide were added. Then 14.372 g of $Fe_2O_3$ powder were added followed by 88.10 g of 32.2 wt % $SiO_2$ sol. The mixture was stirred in an uncovered beaker with heating in order to reduce the volume by evaporation of water. When the mixture could no longer be stirred, it was dried in an oven at 120 ° C. Thereafter it was calcined for 3 hours at 325 ° C., 3 hours at 820 ° C. then at 650 ° C. for an additional 3 hours. Molybdenum was added to 3 g of calcined catalyst, having particle sizes between 20 and 35 mesh, using the incipient wetness method by uniformly wetting it with 1.2 ml of a 10 ml solution containing 0.0162 g of $(NH_4)_6Mo_7O_{24} \cdot 4H_2O$. The treated catalyst was dried at 120° C. then heat treated at 325° C. for 3 hours. The treated catalyst was then contacted with isobutanol in a coarse glass frit funnel by allowing the isobutanol to pass through the funnel without suction. After washing with isobutanol, the catalyst was heated in an oven at 120° C. to remove the residual isobutanol.

Catalyst E (Invention)

30.014 g of $V_2O_5$ powder were added to a solution consisting of 100 ml of 30 wt % $H_2O_2$ in 900 ml of water in a two liter beaker. After reaction of the $V_2O_5$ powder with $H_2O_2$ was complete, 76.959 g of $Sb_2O_3$ were added followed by 1.055 g of $TiO_2$. The beaker was covered with a watch glass and the mixture was stirred and heated for about 3 hours. Then 4.998 g of 19.9 wt % $SnO_2$ sol prepared by dispersing $SnO_2 \cdot xH_2O$ (metastannic acid) in an aqueous solution of tetramethyl ammonium hydroxide were added. Then 15.809 g of $Fe_2O_3$ powder were added, followed by 0.1436 g of $(NH_4)_6Mo_7O_{24} \cdot 4H_2O$, and then followed by 96.919 g of 32.2 wt % $SiO_2$ sol. The mixture was stirred in an uncovered beaker with heating in order to reduce the volume by evaporation of water. When the mixture could no longer be stirred, it was dried in an oven at 120° C. Thereafter it was calcined for 3 hours at 325° C., 3 hours at 820° C. then at 650° C. for an additional 3 hours. The calcined catalyst, having particle sizes between 20 and 35 mesh, was then contacted with isobutanol in a coarse glass frit funnel by allowing the isobutanol to pass through the funnel without suction. After washing with isobutanol, the catalyst was heated in an oven at 120° C. to remove the residual isobutanol.

Catalyst F (Invention)

30.014 g of $V_2O_5$ powder were added to a solution consisting of 100 ml of 30 wt % $H_2O_2$ in 900 ml of water in a two liter beaker. After reaction of the $V_2O_5$ powder with $H_2O_2$ was complete, 76.959 g of $Sb_2O_3$ were added followed by 1.055 g of $TiO_2$. The beaker was covered with a watch glass and the mixture was stirred and heated for about 3 hours. Then 4.998 g of 19.9 wt % $SnO_2$ sol prepared by dispersing $SnO_2 \cdot xH_2O$ (metastannic acid) in an aqueous solution of tetramethyl ammonium hydroxide were added. Then 15.809 g of $Fe_2O_3$ powder were added, followed by 0.2872 g of $(NH_4)_6Mo_7O_{24} \cdot 4H_2O$, and then followed by 96.919 g of 32.2 wt % $SiO_2$ sol. The mixture was stirred in an uncovered beaker with heating in order to reduce the volume by evaporation of water. When the mixture could no longer be stirred, it was dried in an oven at 120° C. Thereafter it was calcined for 3 hours at 325° C., 3 hours at 820° C. then at 650° C. for an additional 3 hours. The calcined catalyst, having particle sizes between 20 and 35 mesh, was then contacted with isobutanol in a coarse glass frit funnel by allowing the isobutanol to pass through the funnel without suction. After washing with isobutanol, the catalyst was heated in an oven at 120° C. to remove the residual isobutanol.

Example G (Comparative)

The following were added to 75.2 lbs of water in a 50 gallon reactor vessel equipped with a mechanical agitator and a temperature controlled water jacket: 84.8 lbs of 20 wt % $SnO_2$ sol prepared by dispersing $SnO_2 \cdot xH_2O$ (metastannic acid) in an aqueous solution of tetramethyl ammonium hydroxide, 8 lbs of a 25% aqueous solution of tetramethyl ammonium hydroxide, 4.45 lbs of $TiO_2$, 51.2 lbs of $V_2O_5$, 114.8 lbs of $Sb_2O_3$, and 4.5 lbs of $Fe_2O_3$. The reactor was sealed and heated to 125° C. for 5 hours with continuous agitation. A portion of the mixture was taken and stirred in an uncovered beaker with heating in order to reduce the volume by evaporation of water. When the mixture could no longer be stirred, it was dried in an oven at 120° C. Thereafter it was calcined for 3 hours at 325° C., 3 hours at 820° C. then at 650° C. for an additional 3 hours. The calcined catalyst, having particle sizes between 20 and 35 mesh, was then contacted with isobutanol in a coarse glass frit funnel by allowing the isobutanol to pass through the funnel without suction. After washing with isobutanol, the catalyst was heated in an oven at 120° C. to remove the residual isobutanol.

Catalyst H (Invention)

The following were added to 75.2 lbs of water in a 50 gallon reactor vessel equipped with a mechanical agitator and a temperature controlled water jacket: 84.8 lbs of 20 wt % $SnO_2$ sol prepared by dispersing $SnO_2 \cdot xH_2O$ (metastannic acid) in an aqueous solution of tetramethyl ammonium hydroxide, 8 lbs of a 25% aqueous solution of tetramethyl ammonium hydroxide, 4.45 lbs of TiO2, 51.2 lbs of V2O5, 114.8 lbs of $Sb_2O_3$, and 4.5 lbs of $Fe_2O_3$. The reactor was sealed and heated to 125° C. for 5 hours with continuous agitation. A portion of the mixture was taken and stirred in an uncovered beaker with heating in order to reduce the volume by evaporation of water. When the mixture could no longer be stirred, it was dried in an oven at 120° C. Thereafter it was calcined for 3 hours at 325° C., then at 650° C. for 3 hours. Molybdenum was added to the catalyst, having particle sizes between 20 and 35 mesh, using the incipient wetness method by taking 10 g of catalyst and uniformly wetting it with 1.5 ml of a 100 ml solution containing 0.3681 g of $(NH_4)_6Mo_7O_{24} \cdot 4H_2O$. The treated catalyst was dried at 120° C. then heat treated at 820 C. for 3 hours then at 650° C. for an additional 3 hours. The calcined catalyst was then contacted with isobutanol in a coarse glass frit funnel by allowing the isobutanol to pass through the funnel without suction. After washing with isobutanol, the catalyst was heated in an oven at 120° C. to remove the residual isobutanol.

EXAMPLE I (Comparative)

The following were added to 75.2 lbs of water in a 50 gallon reactor vessel equipped with a mechanical agitator and a temperature controlled water jacket: 84.8 lbs of 20 wt % $SnO_2$ sol prepared by dispersing $SnO_2 \cdot xH_2O$ (metastannic acid) in an aqueous solution of tetramethyl ammonium hydroxide, 8 lbs of a 25% aqueous solution of tetramethyl ammonium hydroxide, 4.45 lbs of $TiO_2$, 51.2 lbs of $V_2O_5$, 114.8 lbs of $Sb_2O_3$, and 4.5 lbs of $Fe_2O_3$. The reactor was sealed and heated to 125° C. for 5 hours with continuous agitation. The resulting mixture was then spray-dried. The spray-dried catalyst was calcined for 3 hours at 325° C., 3 hours at 820° C. then at 650° C. for an additional 3 hours. The calcined catalyst was then contacted with isobutanol in a coarse glass frit funnel by allowing the isobutanol to pass through the funnel without suction. After washing with isobutanol, the catalyst was heated in an oven at 120° C. to remove the residual isobutanol.

Catalyst J (Invention)

Molybdenum was added to Catalyst I using the incipient wetness method by taking 10 g of Catalyst I and uniformly wetting it with 2 ml of a 100 ml solution containing 0.1 g of $(NH_4)_6Mo_7O_{24}\cdot 4H_2O$. The treated catalyst was dried at 120° C. then heat treated at 300° C. for 1 hour.

Catalyst K (Invention)

Molybdenum was added to Catalyst I using the incipient wetness method by taking 10 g of Catalyst I and uniformly wetting it with 2 ml of a 100 ml solution containing 0.3 g of $(NH_4)_6Mo_7O_{24}\cdot 4H_2O$. The treated catalyst was dried at 120° C. then heat treated at 300° C. for 1 hour.

TABLE I

| | | C. T. | Feed Ratios | | | | % $C_3H_8$ | % Product Selectivities | | | |
|---|---|---|---|---|---|---|---|---|---|---|---|
| Example | Catalyst | (sec) | $C_3H_8$ | $NH_3$ | $O_2$ | $N_2$ | Conv. | Acrylonitrile | $C_3H_6$ | Acrylonitrile + $C_3H_6$ | CO + $CO_2$ |
| Example 1 (Comparative) | A | 0.9 | 3.0 | 0.8 | 2.0 | 2.0 | 19.4 | 58.9 | 0.9 | 59.8 | 25.3 |
| Example 2 (Comparative) | A | 1.0 | 3.0 | 0.8 | 2.0 | 2.0 | 20.2 | 58.3 | 1.1 | 59.4 | 25.4 |
| Example 3 (Invention) | B | 1.1 | 3.0 | 0.8 | 2.0 | 2.0 | 20.2 | 60.3 | 1.3 | 61.7 | 23.5 |
| Example 4 (Invention) | B | 1.1 | 3.0 | 0.8 | 2.0 | 2.0 | 20.6 | 59.9 | 1.2 | 61.1 | 23.2 |
| Example 5 (Invention) | C | 1.2 | 3.0 | 0.8 | 2.0 | 2.0 | 20.7 | 59.7 | 1.1 | 60.8 | 23.3 |
| Example 6 (Invention) | C | 1.4 | 3.0 | 0.8 | 2.0 | 2.0 | 18.2 | 58.3 | 2.5 | 60.8 | 21.9 |
| Example 7 (Invention) | C | 1.1 | 3.0 | 0.8 | 2.0 | 2.0 | 20.0 | 59.9 | 1.3 | 61.2 | 22.7 |
| Example 8 (Invention) | C | 1.1 | 3.0 | 0.8 | 2.0 | 2.0 | 19.2 | 60.2 | 2.0 | 62.2 | 22.0 |
| Example 9 (Invention) | D | 0.7 | 3.0 | 0.8 | 2.0 | 2.0 | 21.8 | 61.2 | 1.6 | 62.9 | 21.1 |
| Example 10 (Invention) | E | 1.2 | 3.0 | 0.8 | 2.0 | 2.0 | 19.5 | 59.5 | 1.4 | 61.0 | 22.4 |
| Example 11 (Invention) | F | 1.5 | 3.0 | 0.8 | 2.0 | 2.0 | 19.7 | 57.6 | 2.5 | 60.1 | 22.6 |
| Example 12 (Comparative) | G | 1.0 | 3.0 | 0.8 | 2.1 | 2.0 | 19.6 | 56.6 | 2.4 | 59.0 | 25.0 |
| Example 13 (Invention) | H | 1.1 | 3.0 | 0.8 | 2.0 | 2.0 | 19.8 | 58.2 | 2.4 | 60.5 | 23.4 |
| Example 14 (Comparative) | I | 1.3 | 3.0 | 0.8 | 2.0 | 2.0 | 19.5 | 53.9 | 2.9 | 56.8 | 27.5 |
| Example 15 (Invention) | J | 1.6 | 3.0 | 0.8 | 2.0 | 2.0 | 19.7 | 55.6 | 2.2 | 57.8 | 26.9 |
| Example 16 (Invention) | K | 1.8 | 3.0 | 0.8 | 2.0 | 2.0 | 19.9 | 57.0 | 3.5 | 60.6 | 24.8 |

What we claim as our invention is:

1. A process for making acrylonitrile or methacrylonitrile by the catalytic reaction in the vapor phase of a paraffin selected from propane and isobutane with molecular oxygen and ammonia by catalytic contact of the reactants in a reaction zone with a catalyst, the feed composition having a mole ratio of the paraffin to ammonia in the range of from about 2.5 to 16 and a mole ratio of paraffin to oxygen in the range of from about 1.0 to 10, wherein said catalyst has the elements in the proportions indicated by the empirical formula:

$$VSb_mA_aMo_bD_dO_x$$

where

A is one or more of Ti, Sn, Fe, Cr and Ga;

D is one or more of Li, Mg, Ca, Sr, Ba, Co, Ni, Zn, Ge, Nb, Zr, W, Cu, Te, Ta, Se, Bi, Ce, In, As, B and Mn;

m equals 0.8 to 4;

a equals 0.01 to 2;

0<b<0.0045;

d is 0 to 2;

x is determined by the oxidation state of the cations present, and the catalyst has been heat treated at a temperature of at least 780° C.

2. The process of claim 1 wherein m ranges from about 1.2 to 2.0.

3. The process of claim 1 wherein A includes one or more of tin, titanium and iron.

4. The process of claim 1 wherein the reaction takes place in a fluid bed reactor.

5. The process of claim 4 wherein any unreacted propane or isobutane is recycled into the fluid bed reactor.

6. The process of claim 1 wherein b ranges from greater than zero to about 0.0035.

7. The process of claim 1 wherein b ranges from greater than zero to about 0.0030.

8. A process for the manufacture of a substantially clump free promoted vanadium-antimony oxide catalyst having the empirical formula set forth in claim 16 comprising incorporating one or more of the required A elements in the catalyst along with the required molybdenum element prior to the calcination of the catalyst, and calcining the catalyst including the A element and molybdenum at a temperature of at least 780° C.

9. The process of claim 8 wherein the molybdenum is added to the catalyst after the catalyst has been calcined at a temperature of at least 780° C.

10. The process of claim 9 wherein the molybdenum is added to the catalyst by uniformly wetting the calcined catalyst with an aqueous solution containing molybdenum, drying the catalyst and heat treating the catalyst.

11. The process of claim 9 wherein the molybdenum is added to the catalyst by impregnating said catalyst with a powder comprising a molybdenum containing material.

12. The process of claim 11 wherein the powder is selected from the group consisting of $MoO_3$ and ammonium molybdate.

* * * * *

UNITED STATES PATENT AND TRADEMARK OFFICE
CERTIFICATE OF CORRECTION

PATENT NO. : 6,156,920
DATED : December 5, 2000
INVENTOR(S) : James Frank Brazdil, Jr., Mark Anthony Toft It is certified that error appears in the above-identified patent and that said Letters Patent is hereby corrected as shown below:

Column 1,
Lines 16 and 17, "have been synthetic resins" should read: "have been industrially produced as important intermediates in the preparation of fibers, synthetic resins"

Column 6,
Line 31, "of $V_2O5$, 114.8 lbs of" should read: "of $V_2O_5$, 114.8 lbs of"
Line 45, "treated at 820C" should read: "treated at 820°C"

Column 8,
Line 46, "set forth in claim 16" should read: "set forth in claim 1"

Signed and Sealed this

Twenty-fifth Day of September, 2001

Attest:

NICHOLAS P. GODICI
Attesting Officer     Acting Director of the United States Patent and Trademark Office